United States Patent
Csörgei et al.

(10) Patent No.: US 9,562,067 B2
(45) Date of Patent: Feb. 7, 2017

(54) PROCESS FOR THE PRODUCTION OF 19-NORPREGN-4-EN-3,20-DIONE-17α-OL(GESTONORONE) AND INTERMEDIATES THEREFOR

(71) Applicant: RICHTER GEDEON NYRT., Budapest (HU)

(72) Inventors: János Csörgei, Budapest (HU); Anita Horváth, Nagykanizsa (HU); Csaba Sánta, Budapest (HU); Sándor Mahó, Budapest (HU); Zoltán Béni, Maglód (HU); János Horváth, Budapest (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 15/038,299

(22) PCT Filed: Dec. 15, 2014

(86) PCT No.: PCT/IB2014/066907
§ 371 (c)(1),
(2) Date: May 20, 2016

(87) PCT Pub. No.: WO2015/092647
PCT Pub. Date: Jun. 25, 2015

(65) Prior Publication Data
US 2016/0297848 A1 Oct. 13, 2016

(30) Foreign Application Priority Data

Dec. 16, 2013 (HU) ..................................... 1300722

(51) Int. Cl.
| C07J 7/00 | (2006.01) |
| C07J 41/00 | (2006.01) |
| C07C 51/00 | (2006.01) |
| C07J 1/00 | (2006.01) |
| C07J 51/00 | (2006.01) |

(52) U.S. Cl.
CPC ............. *C07J 1/0081* (2013.01); *C07J 1/0059* (2013.01); *C07J 7/006* (2013.01); *C07J 41/0094* (2013.01); *C07J 51/00* (2013.01)

(58) Field of Classification Search
CPC .................................. C07J 7/0075; C07J 41/00
See application file for complete search history.

(56) References Cited

U.S. PATENT DOCUMENTS

| 2,781,365 A * | 2/1957 | Rosenkranz | ............... C07J 5/00 540/101 |
| 3,381,003 A | 4/1968 | Patchett et al. | |
| 3,423,435 A | 1/1969 | Klimstra | |
| 3,764,615 A | 10/1973 | Hauser | |
| 8,314,145 B2 * | 11/2012 | Dancsi | ................. C07J 41/0094 514/510 |

FOREIGN PATENT DOCUMENTS

DE 289 540 A5 5/1991

OTHER PUBLICATIONS

Tang et al.: "Stereoselective asymmertric synthesis and characterization of 17alpha-acetoxy-19-nor-progesterone", J. Cent. South Univ. Technol., 2004, vol. 11, No. 3, pp. 300-303.
Claudel et al.: "An Efficient Hemisynthesis of 20- and 21-[13C]-Labeled Cortexolone: A Model for the study of Skin Sensitization of Corticosteroids", Synthesis, 2009, No. 20, pp. 3391-3398.
Arbez-Gindre et al.: "Methyl exchange on silicon during the addition of methylmagnesium iodide to a cyanohydrin O-silyl ether", Chem. Commun, 1999, No. 5, pp. 431-432.
Popova et al.: "Synthesis of Pregnane Derivatives", Chemistry of Natural Compounds, 1984, vol. 20, No. 3, pp. 302-304.

* cited by examiner

*Primary Examiner* — Paul A Zucker
(74) *Attorney, Agent, or Firm* — Jason D. Voight

(57) ABSTRACT

The present invention relates to a new stereoselective process for the synthesis of 17(α)-17-acetyl-17-hydroxy-estr-4-en-3-one of formula (I), as well as to the new intermediates of the process. The 17(α)-17-acetyl-17-hydroxy-estr-4-en-3-one (gestonorone) is an important intermediate in the synthesis of the active ingredients having progestogen activity—such as gestonorone capronate and nomegestrol acetate. Formulas (I), (II) and (III).

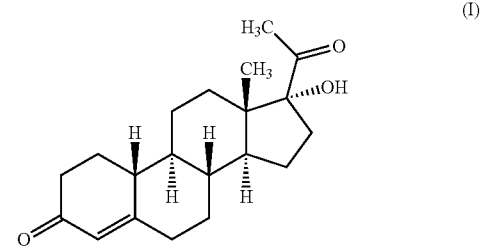

(I)

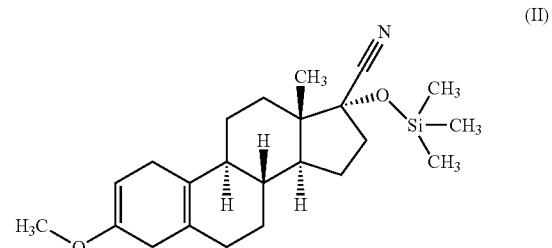

(II)

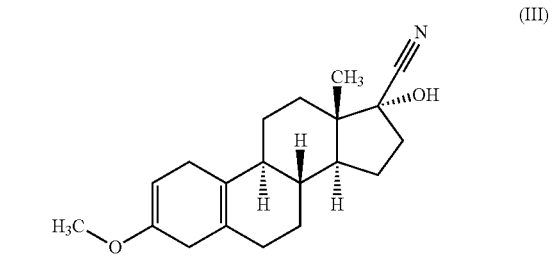

(III)

20 Claims, 2 Drawing Sheets

--Prior Art--

--Prior Art--

--Prior Art--

--Prior Art--

PROCESS FOR THE PRODUCTION OF 19-NORPREGN-4-EN-3,20-DIONE-17α-OL(GESTONORONE) AND INTERMEDIATES THEREFOR

This is the national stage of International Application PCT/IB2014/066907, filed Dec. 15, 2014.

The present invention relates to a new stereoselective process for the synthesis of 17(α)-17-acetyl-17-hydroxy-estr-4-en-3-one of formula (I) using the compound of formula (IV) as starting material, as well as to the new intermediates of the process.

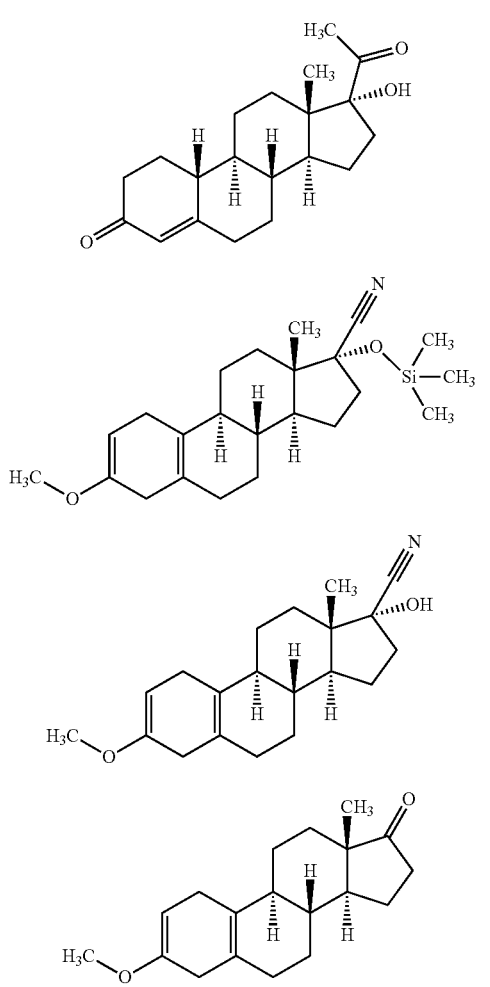

BACKGROUND OF THE INVENTION

The 17(α)-17-acetyl-17-hydroxy-estr-4-en-3-one (hereafter: gestonorone) is an important intermediate in the synthesis of the active ingredients having progestogen activity—such as gestonorone capronate and nomegestrol acetate. There are various known processes in the literature for its synthesis. The first was described in 1953 (MXX762308, U.S. Pat. No. 2,781,365; GB 762,308). In this process the gestonorone was synthesized starting from 17-acetyl-3-hydroxy-estra-1,3,5(10),16-tetraene via a derivative of 17β-acetyl-17α-hydroxy-3-methoxy-estra-1,3,5(10)-triene protected in position 20 with ethylene ketal.

In the U.S. Pat. No. 3,381,003 the gestonorone is synthesized starting from estron-3-alkyl ether (FIG. 1.). The pregnane side-chain in position 17 is synthesized in a complicated and time-consuming 7-step process. The oxo group in position 20 is protected as ethylene ketal, then the necessary transformations are carried out on the A-ring.

The estron-3-alkyl ether is ethynylated in position 17, the 17 hydroxyl group of the obtained compound is acylated and the ethynyl group is brominated with N-bromo-acetamide in an organic solvent in the presence of tert-butanol and water. In the next debromination reaction the 17α-acetyl-3-alkoxy-17β-hydroxy-gona-1,3,5(10)-trien-17β-yl-acetate is formed in the presence of zinc and acetic acid, which is then reduced with calcium metal in liquid ammonia. The isopregnane side-chain of the obtained compound is isomerized in acetic acid in the presence of zinc at reflux temperature for 24 h. The hydroxyl group in position 17 is introduced the following way: the oxo group in position 20 is transformed into enol acetate with acetic anhydride in the presence of catalytic amount of p-toluenesulfonic acid and the formed $\Delta^{17(20)}$-double bond is oxidized with perbenzoic acid. Finally the oxo group in position 20 is transformed into ethylene ketal with ethylene glycol in the presence of catalytic amount of p-toluenesulfonic acid. The next two reaction steps are carried out as described in point 1, the derivative of 17β-acetyl-17α-hydroxy-3-methoxy-estra-1,3,5(10)-triene protected in position 20 with ethylene ketal is reduced with lithium metal in liquid ammonia and the obtained compound is transformed into gestonorone with acid hydrolysis.

According to the U.S. Pat. No. 3,423,435 17-cyano-17-hydroxy-3-methoxy-estra-2,5(10)-diene (a mixture of isomers/diastereomers) is synthesized starting from 3-methoxy-estra-2,5(10)-dien-17-one with acetone cyanohydrin, which is acylated with acetic anhydride in pyridine (FIG. 2.). The synthesis of cyanohydrin is also described starting from 19-nor-androsten-dione.

During the two processes below the 17α-hydroxy-pregnane side-chain is synthesized starting from estr-4-en-3-one or an estr-4-en-3-one derivatives.

In the U.S. Pat. No. 3,764,615 the synthesis of the 17α-hydroxy-pregnane derivatives is described (FIG. 3.). The pregnane side-chain is synthesized via the sulfite ester derivatives of 17α-ethynyl-17β-hydroxy steroids the following way: the ethynyl group is transformed into pregnane side-chain via hydration in the presence of mercury salt. The disadvantage of the process is the use of environmental pollutant mercury salt.

In the Chinese article published in Journal of Central South University of Technology (English Edition) (2004), 11(3), 300-303 estr-4-en-3-on-17-cyanohydrine is synthesized from estr-4-en-3,17-dione with potassium cyanide in aqueous methanol, then the oxo group of the obtained product is protected as ketal using ethylene glycol and boron trifluoride as catalyst. The tertiary hydroxyl group is protected with butyl vinyl ether and the pregnane side-chain is formed with methyl lithium in diethyl ether as solvent. The protective groups are removed with hydrochloric acid hydrolysis. The overall yield of the six-step process is 63% (FIG. 4.).

SUMMARY OF THE INVENTION

During our experiments surprisingly it was found, that the pregnane side-chain can be synthesized in much fewer steps and under milder reaction conditions as compared to the above described processes. A cyanohydrine precursor compound with the proper steric arrangement is required for the formation of the pregnane side-chain. The β-cyanohydrine of formula (III) is obtained from the starting material in high epimeric purity, then the hydroxyl group in position 17 is protected as silyl ether. Although the starting material contains an acid labile enol ether moiety, but the silyl ether type protective group in position 17 can be synthesized under neutral reaction conditions used in our process.

The process can also be applied in those cases when the compounds contain acid labile moieties (for example enol ether), while the alkoxy ether type protective groups are not suitable for this purpose.

The basis of our invention is the discovery, that the silyl ether protected cyanohydrines can be reacted with methyl lithium under proper reaction conditions and the pregnane side-chain can simply be synthesized.

The starting material, the 3-methoxy-estra-2,5(10)-dien-17-one of formula (IV), which can be synthesized for example according to the process described in the U.S. Pat. No. 3,423,435 (from estron-3-methylether with Birch reduction) or from other aromatic intermediate with Birch reduction and oxidation, can easily be transformed into 3-oxo-4-ene derivative, on the other hand it has an appropriate protective group, therefor (17α)-17-acetyl-17-hydroxy-estr-4-en-3-one of formula (I) can be synthesized in fewer reaction steps. Because of the mild reaction conditions there is no need to use selective protective groups such as ketal or enol ether type protective groups in contrast to the synthesis starting from 3-oxo-4-ene intermediate.

It is also advantageous that under appropriately selected reaction conditions the 17α-hydroxy-17β-nitril (β-cyanohydrine) of formula (III) is obtained from compound (IV) in excellent yield and in high epimeric purity. The explanation of this is that in the first phase of the reaction the amount of the starting material is reduced to less than 1% by choosing the right special reaction conditions, then in the second phase of the reaction the crystallization of the β-cyanohydrine is induced from the formed isomeric mixture of cyanohydrine by proper selection of the reaction conditions, this way the equilibrium of the isomerization reaction is shifted towards the β-cyanohydrine.

The methylation of cyanohydrine of formula (II) preferably protected in position 17 with silyl ether can not be carried out with methyl lithium, in fact only by-products are formed under harsh reaction conditions too. If a suitable complex-forming agent, for example tetraalkyl ethylendiamine, preferably N,N,N',N'-tetramethylethylendiamine, is used to transform the reagent containing methyl lithium oligomers into monomers, the methylation reaction of cyanohydrine protected in position 17 with silyl ether can be carried out in good yield and in good quality.

The invention also relates to the intermediates of formula (II) and (III) of the process.

According to the above mentioned facts the strategy of our synthesis was so elaborated that the requirements of the guidelines for planning a modern industrial synthesis of steroids were taken into consideration and best fulfilled.

The process of our invention is more simple and shorter and the obtained final product fulfills the high quality requirements owing to the properly chosen starting material.

DETAILED DESCRIPTION OF THE INVENTION

Figure 1:
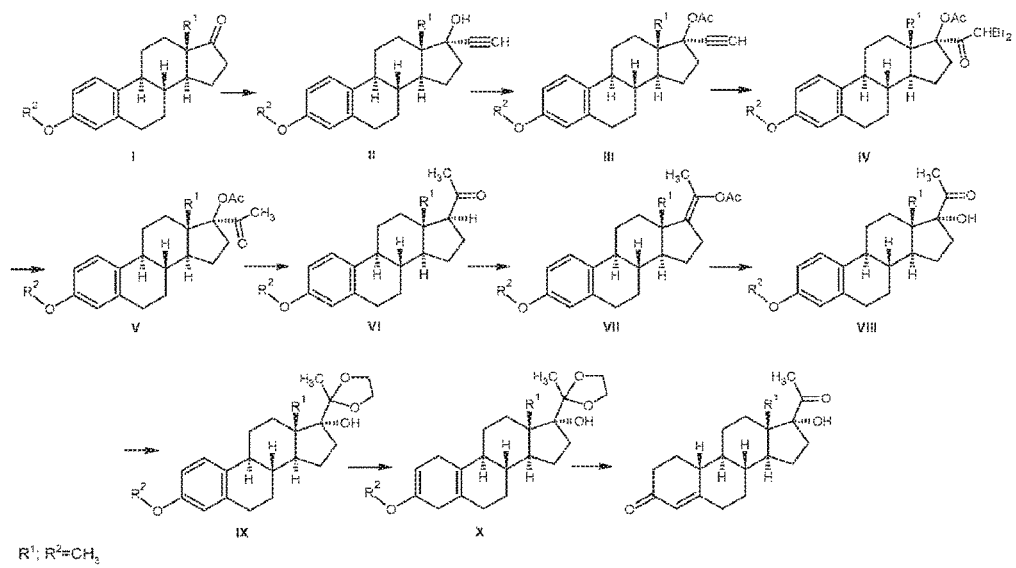
FIG. 1 is a flowchart showing the synthesis of gestonorone starting from estron-3-alkyl ether as disclosed in U.S. Pat. No. 3,381,003.
Figure 2:
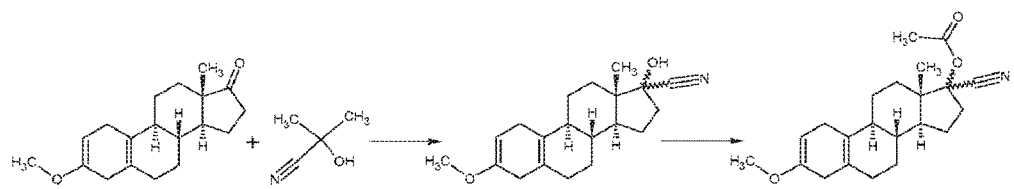
FIG. 2 is a flowchart showing the synthesis of 17-cyano-17-hydroxy-3-methoxy-estra-2,5(10)-diene starting from 3-methoxy-estra-2,5(10)-dien-17-one with acetone cyanohydrin as disclosed in U.S. Pat. No. 3,423,435.
Figure 3:
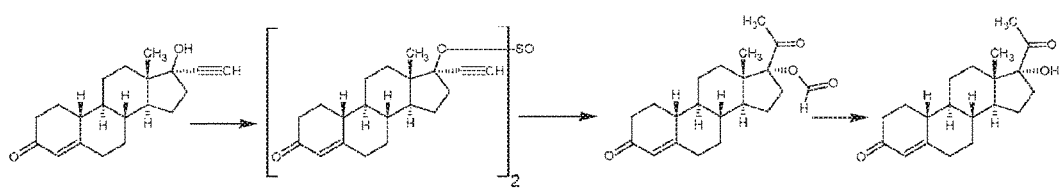
FIG. 3 is a flowchart showing the synthesis of 17α-hydroxy-pregnane derivatives as disclosed in U.S. Pat. No. 3,764,615.
Figure 4:
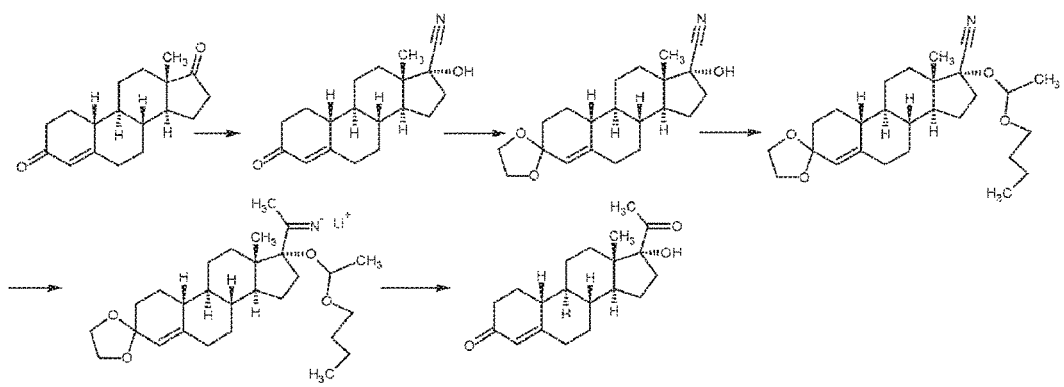
FIG. 4 is a flowchart showing the synthesis of estr-4-en-3-on-17-cyanohydrine from estr-4-en-3,17-dione as shown in Journal of Central South University of Technology (English Edition) (2004), 11(3), 300-303.
Figure 5:
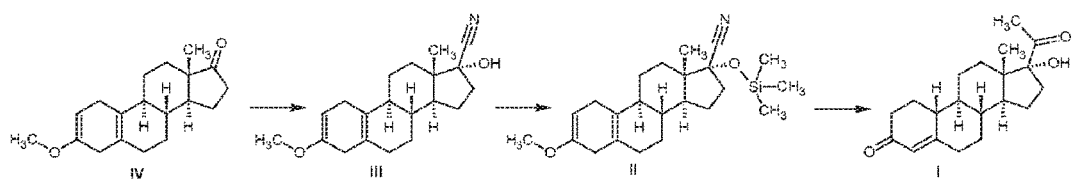
FIG. 5 is a flowchart showing the process of the present invention.

The process of our invention (FIG. 5.) is described in detail hereunder.

The synthesis of compound (III) from compound (IV) is carried out the following way:

Short-chain aliphatic alcohols, preferably methanol or ethanol are used as solvent.

Alkali cyanides, preferably potassium or sodium cyanides are used as reagents, the molar ratio is selected between 1.5-10, preferably between 2-4 mol, and a mild organic acid, preferably acetic acid is used as further reagent for liberating hydrogen cyanide, the molar ratio is selected between 1.3-8, preferably between 1.5-3 mol.

The temperature of the reaction is kept between +20-+63° C., preferably the temperature program described in Example 1 is kept.

The synthesis of compound (II) from compound (III) is carried out the following way:

Ethers, for example diethyl ether, tetrahydrofuran, methyl tert-butyl ether, diisopropyl ether, preferably methyl tert-butyl ether or tetrahydrofuran are used as solvent.

Trimethyl chlorosilane is used as reagent in the presence of imidazole, the molar excess of the reagent is between 2-10 mol, preferably 2.5-4 mol.

The temperature of the reaction is kept between 0-+40° C., preferably between 0-+10° C.

The synthesis of compound (I) from compound (II) is carried out the following way:

Ethers or formaldehyde dialkylacetals, for example diethyl ether, tetrahydrofuran, methyltetrahydrofuran, methyl tert-butyl ether, diisopropyl ether, diethoxymethane, dimethoxymethane, preferably methyl tert-butyl ether, tetrahydrofuran or diethoxymethane are used as solvent.

The excess of methyl lithium reagent can be 1.5-10 mol equivalent, preferably 2.5-5 mol equivalent.

The stability of methyl lithium oligomers can be reduced with substituted 1,2-diamino-ethanes, preferably with N,N,N',N'-tetramethylethylendiamine.

The temperature of the reaction is kept between −78 and −10° C., preferably between −40 and −20° C.

The protected imine obtained as intermediate is transformed into the final product of formula (I) with mineral acids or strong organic acids, for example with hydrochloric acid, sulfuric acid, potassium hydrogensulfate, sodium hydrogensulfate, p-toluenesulfonic acid, perchloric acid, preferably with hydrochloric acid.

During the hydrolysis alcohols or ethers, preferably methanol, ethanol or methyl tert-butyl ether, diethoxymethane, tetrahydrofuran are used as solvent.

The hydrolysis is carried out at a temperature between 0° C. and the boiling point of the applied solvent, preferably between +5 and +40° C.

The process of our invention is illustrated by the following not limiting examples.

Example 1

Synthesis of (17α)-hydroxy-3-methoxyestra-2,5(10)-dien-17-carbonitrile

Under inert atmosphere 50.0 g of 3-methoxyestra-2,5(10)-dien-17-one was suspended in 500 ml of ethanol and 34.25 g of potassium cyanide and 0.15 g of 2,6-ditert-butyl-4-methyl-phenol were added while stirring. After 10 minutes stirring 20.0 ml of acetic acid was added dropwise over a period of 10 minutes. The reaction mixture was warmed from 30-35° C. to 58-63° C., stirred at this temperature for 1 h, then cooled to 20-25° C. and stirred for 16 h. 50 ml of water was added to the reaction mixture and the slurry was stirred for 1 h. The precipitated crystals were filtered off, suspended with 5×150 ml of water, and washed with 2×100 ml of water. The wet crystals were stirred under inert atmosphere with 300 ml of ion-exchanged water for 15 minutes, filtered off and washed with 2×100 ml of water. The wet crystals were washed with 75 ml of cold ethanol and 3×50 ml of methyl tert-butyl ether.

Yield: 53.0 g (96.9%)
Purity (HPLC): 97.49%
$^1$H NMR (DMSO-d6, 500 MHz) δ: 6.26 (s, 1H), 4.64 (t, J=3.3 Hz, 1H), 3.45 (s, 3H), 2.70-2.87 (m, 1H), 2.49-2.63 (m, 2H), 2.37-2.49 (m, 1H), 2.22-2.34 (m, 1H), 1.97-2.08 (m, 1H), 1.76-1.96 (m, 3H), 1.61-1.75 (m, 4H), 1.51-1.60 (m, 1H), 1.37-1.47 (m, 1H), 1.24-1.36 (m, 2H), 1.11-1.25 (m, 2H), 0.83 (s, 3H)
$^{13}$C NMR (DMSO-d6, 125 MHz) δ: 151.8, 127.3, 124.3, 121.8, 90.4, 76.5, 53.4, 48.9, 46.6, 44.3, 38.7, 37.4, 33.6, 29.8, 27.8, 26.9, 24.6, 22.9, 16.2

Example 2

Synthesis of (17α)-3-methoxy-17-[(trimethylsilyl)-oxy]-2,5(10)-dien-17-carbonitrile Under inert atmosphere to a stirred mixture of 53.0 g of (17α)-17-hydroxy-3-methoxyestra-2,5(10)-dien-17-carbonitrile, 0.15 g of 2,6-ditert-butyl-4-methyl-phenol and 900 of methyl tert-butyl ether a solution of 36.0 g of imidazole in 100 ml of tetrahydrofuran was added. The reaction mixture was cooled to 0-5° C. and 60.0 ml of trimethylchlorosilane was added dropwise at such a rate to keep the temperature below 5° C. After stirring for 2 h 50 ml of water was added to the reaction mixture and after 10 minutes stirring the organic phase was separated and washed with 3×50 ml of water. The organic phase was dried over 7.5 g of MgSO4, filtered and the filtered drying agent was washed with 2×25 ml of methyl tert-butyl ether. The filtrate was concentrated to half volume, and 3×300 ml of methyl tert-butyl ether was distilled off at 30-35° C. The solution was diluted to 600 nil and used in the next step.

Dry substance content: 58.9 g (90.4%)
Water content: 0.09 g/100 ml
Purity (HPLC): 96.53%
$^1$H NMR (CD$_2$Cl$_2$, 500 MHz) δ: 4.65 (t, J=3.3 Hz, 1H), 3.50-3.57 (m, 3H), 2.80-2.95 (m, 1H), 2.56-2.69 (m, 2H), 2.45-2.55 (m, 1H), 2.33-2.41 (m, 1H), 2.09 (br. s., 1H), 2.01 (ddd, J=14.8, 9.2, 5.6 Hz, 1H), 1.95 (dd, J=13.3, 2.8 Hz, 1H), 1.90 (dd, J=6.4, 0.7 Hz, 1H), 1.76-1.84 (m, 1H), 1.60-1.76 (m, 4H), 1.49-1.55 (m, 1H) 1.33-1.44 (m, 2H), 1.20-1.32 (m, 2H), 0.92 (s, 3H), 0.25 (s, 9H)
$^{13}$C NMR (CD$_2$Cl$_2$, 125 MHz) δ: 153.1, 128.1, 125.4, 121.6, 91.0, 79.4, 54.2, 51.0, 47.6, 45.3, 40.0, 39.5, 34.6, 31.0, 30.8, 28.8, 27.9, 25.8, 24.0, 16.7, 1.3

Example 3

Synthesis of (17α)-17-acetyl-17-hydoxy-estr-4-en-3one

The stirred solution of (17α)-3-methoxy-17-[(trimethysilyl)-oxy]-estr-2,5(10)-dien-17-carbonitrile in 600 ml of methyl tert-butyl ether was cooled to –40° C., then 80 ml of N,N,N',N'-tetramethylethylendiamine and 180 ml of methyl lithium solution (3M in diethoxymethane) were added at such a rate to keep the temperature below –30° C. The reaction mixture was stirred at this temperature for 1 h, then poured into 1000 ml of 4N hydrochloric acid solution cooled to –15-(–10)° C. with intensive cooling. The reaction mixture was stirred at 20-25° C. for 16 h, then the pH of the solution was adjusted to 4-5 by the addition of about 800 ml of 3M sodium acetate. The volatile organic components were distilled off and the residue was stirred at 20-25° C. for 1 h. The precipitated crude product was filtered off, suspended with 5×500 ml of water, washed with 100 ml of cold methanol, and dried in vacuum oven.

Yield: 32.42 g (67.1%)
Purity (HPLC): 89.66%
Under inert atmosphere 32.42 g of crude product was added to 97 ml of methanol at 60° C., after a clear solution was obtained the mixture was cooled to 20-25° C. 16.2 ml of water was added to the stirred slurry over a period of 2-3 minutes, then it was cooled to 0-5° C. After stirring for 1 h, the crystals were filtered off, suspended with a mixture of 11.2 ml of water and 67.1 ml of methanol, then dried in vacuum oven.

Yield: 25.67 g (79.2%)
Purity (HPLC): 98.47%
$^1$HNMR (CDCl$_3$, 800 MHz) δ: 5.82-5.85 (m, 1H), 2.85 (s, 1H), 2.69 (ddd, J=14.9, 11.5, 3.1 Hz, 1H), 2.47-2.51 (m, 1H), 2.39-2.43 (m, 1H), 2.28 (s, 3H), 2.23-2.31 (m, 3H), 2.06-2.11 (m, 1H), 1.89-1.93 (m, 1H), 1.81-1.88 (m, 2H), 1.72-1.80 (m, 2H), 1.61 (ddd, J=15.2, 9.2, 6.3 Hz, 1H), 1.52-1.58 (m, 1H), 1.35-1.44 (m, 3H), 1.22-1.29 (m, 1H), 1.12-1.18 (m, 1H), 0.90 (dtd, J=12.0, 10.6, 4.2 Hz, 1H), 0.78 (s, 3H)
$^{13}$C NMR (CDCl$_3$, 201 MHz) δ: 211.6, 199.9, 166.4, 124.6, 89.8, 49.2, 49.0, 48.4, 42.4, 40.2, 36.5, 35.5, 33.5, 31.1, 30.0, 27.9, 26.6, 25.9, 23.8, 15.5

The invention claimed is:
1. A process for the synthesis of (17α)-17-acetyl-17-hydoxy-estr-4-en-3-one of formula (I)

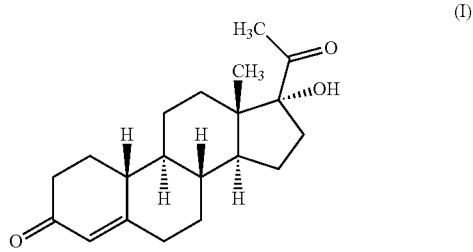

characterized by reacting the compound of formula (II)

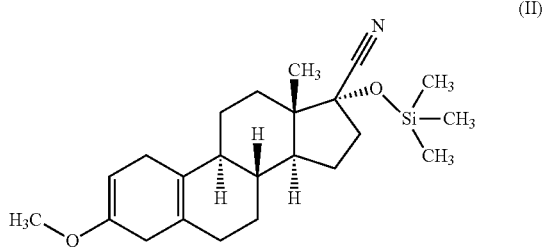

with 1.5-10 mol equivalent of methyl lithium in the presence of substituted 1,2-diamino-ethane in an ether or formaldehyde dialkylacetal solvent or a mixture thereof at a temperature between −78° and −10° C., then reacting the protected imine derivative obtained as intermediate with mineral acids or strong organic acids at a temperature between 0° C. and the boiling point of the applied organic solvent.

2. The process according to claim 1, characterized by synthesizing the compound of formula (II) the following way:
i) reacting the compound of formula (IV)

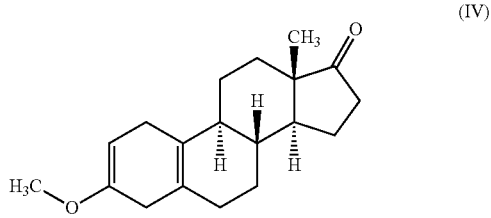

with 1.5-10 mol equivalent of alkali cyanide in a short-chain aliphatic alcohol solvent in the presence of a mild organic acid, then
ii) reacting the obtained compound of formula (III)

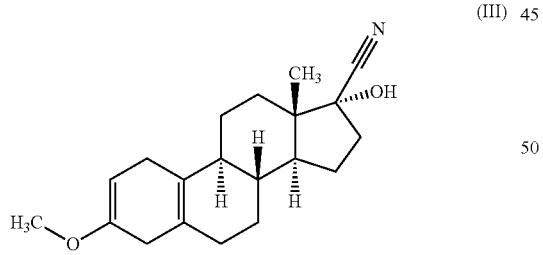

with 2-10 mol equivalent of trimethylchlorosilane in the presence of imidazole in an ether solvent at a temperature between 0 and +40° C.

3. The process according to claim 2, characterized by carrying out the reaction in step i) in ethanol.

4. The process according to claim 2, characterized by using potassium cyanide or sodium cyanide as reagent in step i).

5. The process according to claim 2, characterized by using 2-4 mol excess of cyanide reagent in step i).

6. The process according to claim 2, characterized by using acetic acid as mild organic acid in step i).

7. The process according to claim 2, characterized by using 1.5-3 mol excess of acetic acid in step i).

8. The process according to claim 2, characterized by carrying out the reaction in step ii) at a temperature between 0 and +10° C.

9. The process according to claim 2, characterized by carrying out the reaction in step ii) in methyl tert-butyl ether or tetrahydrofuran.

10. The process according to claim 2, characterized by using 2.5-4 mol excess of reagent in step ii).

11. The process according to claim 1, characterized by using 2.5-5 mol excess of methyl lithium.

12. The process according to claim 1, characterized by using N,N,N',N'-tetramethylethylendiamine as substituted 1,2-diamino-ethane.

13. The process according to claim 1, characterized by carrying out the reaction at a temperature between −40 and −20° C.

14. The process according to claim 1, characterized by using hydrochloric acid in the transformation of the protected imine obtained as intermediate into the compound of formula (I).

15. The process according to claim 1, characterized by carrying out the transformation of the protected imine obtained as intermediate into the compound of formula (I) in a mixture of water and tert-butyl methyl ether, or diethoxymethane as solvent.

16. The process according to claim 1, characterized by carrying out the hydrolysis and acidic rearrangement at a temperature between +5 and +40° C.

17. (17α)-3-methoxy-17-[(trimethylsilyl)-oxy]-estr-2,5(10)-dien-17-carbonitrile of formula (II)

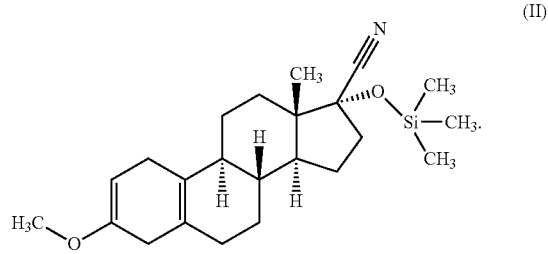

18. A process for the synthesis of (17α)-3-methoxy-17-[(trimethylsilyl)-oxy]-estr-2,5(1.0)-dien-17-carbonitrile of formula (II) of claim 17 characterized by reacting the compound of formula (III)

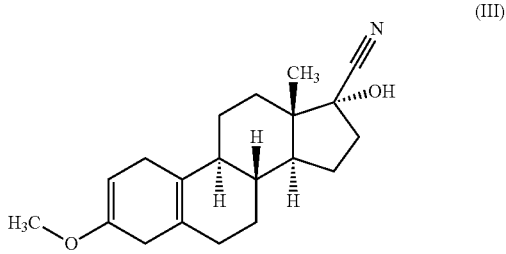

with 2-10 mol equivalent of trimethylchlorosilane in the presence of imidazole in an ether solvent at a temperature between 0 and +40° C.

19. (17α)-17-hydroxy-3-methoxyestra-2,5(10)-dien-17-carbonitrile of formula (III)
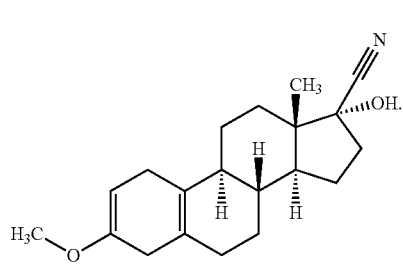
20. A process for the synthesis of (17α)-17-hydroxy-3-methoxyestra-2,5(10)-dien-17-carbonitrile of formula (III) of claim 19 characterized by reacting the compound of formula (IV)
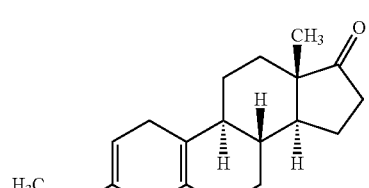
with 1.5-10 mol equivalent of alkali cyanide in a short-chain aliphatic alcohol typo solvent in the presence of a mild organic acid.
* * * * *